United States Patent [19]

Neuzil et al.

[11] 3,998,901
[45] Dec. 21, 1976

[54] SEPARATION OF ETHYLBENZENE WITH AN ADSORBENT COMPRISING SR AND K EXCHANGED X OR Y ZEOLITE

[75] Inventors: Richard W. Neuzil, Downers Grove; Donald H. Rosback, Elmhurst, both of Ill.

[73] Assignee: Universal Oil Products Company, Des Plaines, Ill.

[22] Filed: July 14, 1975

[21] Appl. No.: 595,837

[52] U.S. Cl. .............................. 260/674 SA; 210/24; 210/30 R
[51] Int. Cl.² .................. C07C 15/28; C07C 15/30
[58] Field of Search ................ 210/24; 252/455 Z; 260/674 SA; 208/310 Z

[56] References Cited
UNITED STATES PATENTS

| | | | |
|---|---|---|---|
| 3,686,342 | 8/1972 | Neuzil | 260/674 SA |
| 3,734,974 | 5/1973 | Neuzil | 260/674 SA |
| 3,917,734 | 7/1974 | de Rosset | 252/455 Z |

Primary Examiner—Charles N. Hart
Assistant Examiner—Ethel R. Cross
Attorney, Agent, or Firm—James R. Hoatson, Jr.; Thomas K. McBride; William H. Page, II

[57] ABSTRACT

An adsorptive separation process for separating ethylbenzene from a feed mixture comprising ethylbenzene and a plurality of xylene isomers which process comprises contacting the feed mixture with an adsorbent comprising strontium and potassium exchanged type X or type Y zeolite, selectively adsorbing substantially all of the said xylene isomers to the substantial exclusion of the ethylbenzene and thereafter recovering high-purity ethylbenzene. A desorption step may be used to desorb the adsorbed xylene isomers. The process can be either in the liquid or vapor phase.

27 Claims, No Drawings

SEPARATION OF ETHYLBENZENE WITH AN ADSORBENT COMPRISING SR AND K EXCHANGED X OR Y ZEOLITE

BACKGROUND OF THE INVENTION

1. Field of the Invention

The field of art to which the claimed invention pertains is solid-bed adsorptive separation. More specifically, the invention relates to a process for the separation of ethylbenzene from a feed mixture comprising ethylbenzene and xylene isomers which process employs a solid adsorbent which selectively removes the xylene isomers from the feed material thereby producing a fluid raffinate stream comprising ethylbenzene.

2. Description of the Prior Art

It is well known in the separation art that certain crystalline aluminosilicates can be used to separate hydrocarbon species from mixtures thereof. The separation of normal paraffins from branched chained paraffins for example can be accomplished by using a type A zeolite which has pore openings from 3 to about 5 Angstroms. Such a separation process is disclosed in U.S. Pat. Nos. 2,985,589 and 3,201,491. These adsorbents allow a separation based on the physical size differences in the molecules by allowing the smaller or normal hydrocarbons to be passed into the cavities within the zeolitic adsorbent, while excluding the larger or branched chain molecules.

U.S. Pat. Nos. 3,265,750 and 3,510,423 for example disclose processes in which larger pore diameter zeolites such as the type X or type Y structured zeolites can be used to separate olefinic hydrocarbons.

In addition to separating hydrocarbon types the type X or type Y zeolites have also been employed in processes to separate individual hydrocarbon isomers. In the process described in U.S. Pat. No. 3,114,782, for example, a particular zeolite is used as an adsorbent to separate alkyl-trisubstituted benzene; and in U.S. Pat. No. 3,668,267 a particular zeolite is used to separate specific alkyl-substituted naphthalenes.

Because of the commercial importance of para-xylene, the more well-known and extensively used hydrocarbon isomer separation processes are those for separating para-xylene. Para-xylene is used in the manufacture of terephthalic acid which in turn is subsequently employed in the manufacture of various synthetic fibers such as Dacron, a trademarked product of the duPont Company. In processes described in U.S. Pat. Nos. 3,558,732 and 3,686,342 for example adsorbents comprising particular zeolites are used to separate para-xylene from feed mixtures comprising para-xylene and at least one other xylene isomer by selectively adsorbing para-xylene over the other xylene isomers. In such processes the adsorbents used are para-xylene selective; para-xylene is selectively adsorbed and recovered as an extract component while the rest of the xylenes and ethylbenzenes are all relatively unadsorbed with respect to para-xylene and are recovered as raffinate components.

In the process described in our assignee's application Ser. No. 459,251, now U.S. Pat. No. 3,917,734 issued to A. J. deRosset, ethylbenzene is recovered in high purity from a feed mixture comprising ethylbenzene and xylene isomers. The process basically comprises contacting the feed mixture with an adsorbent comprising calcium exchanged type X or type Y zeolites, selectively adsorbing the xylene isomers, and thereafter recovering ethylbenzene as a raffinate component. The adsorbent employed is thus all-xylene selective rather than para-xylene selective as are the adsorbents used in the para-xylene separation process. The adsorbed xylenes may then be recovered, in one embodiment, by contacting the adsorbent with a desorbent material, preferably comprising toluene, thereby desorbing the xylenes and then withdrawing the desorbed xylenes from the adsorbent. In another embodiment the adsorption and desorption are done continuously in a simulated moving bed countercurrent flow system, the operating principles and sequence of which are described in U.S. Pat. No. 2,985,589. We have discovered that when the feed mixture to this process includes para-xylene and when the preferred toluene desorbent material is employed, the selectivity of that adsorbent is higher for the toluene desorbent material than it is for para-xylene. This results in the inability of that process to obtain high purity product and high yields simultaneously when the ethylbenzene concentration of the feed is about the same as or less than that of para-xylene.

The process of our invention, in one of its embodiments, eliminates that problem. Specifically, we have found that adsorbents comprising strontium and potassium exchanged type X or type Y zeolites exhibit selectivity for all the xylene isomers with respect to ethylbenzene and also have the desired higher selectivity for para-xylene than for toluene thereby making separation of ethylbenzene from xylene isomers in both high purity (98% or greater, expressed as a percent of $C_8$ aromatics present) and high yields (95% or greater) possible for any ethylbenzene concentration in the feed.

Ethylbenzene, used as a raw material in the production of styrene monomer, is commercially produced from the alkylation of benzene with ethylene. The cost of and competing demands for necessary benzene and ethylene feed streams have, however, prompted new efforts to recover ethylbenzene from various $C_8$ aromatic feed streams which already contain ethylbenzene. Such feed streams for instance include $C_8$ aromatic extracts produced by a typical solvent extraction process for a pyrolysis gasoline or from a naphtha which has been reformed with a platinum-halogen-containing catalyst. Additionally, $C_8$ aromatic cuts of hydrogenated pyrolysis naphthas or reformates prepared by fractionation without solvent extraction contain varying amounts of ethylbenzene. The particular utility of the process of our invention therefore is that it offers a method for recovering ethylbenzene from a feed stream which already contains ethylbenzene.

Ethylbenzene can, of course, be separated from the xylene isomers by fractionation but because its boiling point is within about 4° F. of that of para-xylene, the fractionation can be achieved only with the more intricate super-fractionators. Typical ethylbenzene fractionators contain 300 to 400 actual trays and require about a 25-50 to 1 reflux to feed ratio. The process of our invention therefore offers a competitive alternative to the separation of ethylbenzene by super-fractionation

SUMMARY OF THE INVENTION

It is, accordingly, a broad objective of our invention to provide a process for the separation of high-purity ethylbenzene at high recoveries from a feed mixture comprising ethylbenzene and a plurality of xylene isomers. It is a further objective that our process shall apply to such a feed mixture containing any concentration of ethylbenzene.

In brief summary, our invention is, in one embodiment, a process for separating ethylbenzene from a feed mixture comprising ethylbenzene and a plurality of xylene isomers which process comprises contacting said mixture with an adsorbent comprising strontium and potassium exchanged type X or type Y zeolites, selectively adsorbing substantially all of said xylene isomers to the substantial exclusion of ethylbenzene, and thereafter recovering ethylbenzene as a raffinate component.

Our invention is, in another embodiment, a process for separating ethylbenzene from a hydrocarbon feed mixture comprising ethylbenzene and a plurality of xylene isomers which process comprises the steps of: contacting said mixture with an adsorbent comprising strontium and potassium type X or type Y zeolite at adsorption conditions to effect the selective adsorption of substantially all of the xylene isomers to the substantial exclusion of ethylbenzene; withdrawing from the adsorbent a raffinate stream comprising less selectively adsorbed ethylbenzene; contacting the adsorbent at desorption conditions with a desorbent material having a boiling point substantially different from that of the feed mixture to effect the removal of the selectively adsorbed xylene isomers; and, withdrawing from the solid adsorbent bed an extract stream comprising the xylene isomers.

Other embodiments and objects of the present invention encompass details about feed mixtures, adsorbents, desorbents, and operating conditions all of which are hereinafter disclosed in the following discussion of each of these facets of the present invention.

DESCRIPTION OF THE INVENTION

Feed mixtures which can be utilized in the process of this invention will comprise ethylbenzene and a plurality of xylene isomers. Mixtures containing substantial quantities of ethylbenzene and the xylene isomers generally are produced by reforming and isomerization processes, processes which are well known to the refining and petrochemical arts. In reforming processes, a naphtha feed is contacted with a platinum-halogen-containing catalyst at severities selected to produce an effluent containing $C_8$ aromatic isomers. Generally the reformate is then fractionated to concentrate the $C_8$ aromatic isomers in a $C_8$ fraction which may then be further concentrated by solvent extraction processes. Xylene isomerization processes isomerize at isomerization conditions a xylene mixture which is deficient in one or more isomers to produce an effluent containing approximately equilibrium quantities of the $C_8$ aromatic isomers. The equilibrium compositions of the xylene isomers and ethylbenzene at various temperatures are shown in Table 1 below.

Table 1

| Equilibrium $C_8$ Aromatic Compositions* | | | |
|---|---|---|---|
| Temperature, ° C. | 327 | 427 | 527 |
| Mole percent of isomers | | | |
| Ethylbenzene | 6 | 8 | 11 |
| Para-xylene | 22 | 22 | 21 |
| Meta-xylene | 50 | 48 | 45 |
| Ortho-xylene | 22 | 22 | 23 |

*Base on API sources

Feed streams to the process of our invention can contain any two or all three of the xylene isomers in addition to ethylbenzene. Extracted and unextracted $C_8$ reformate fractions and isomerates from xylene isomerization processes containing all of the xylene isomers can be charged as feed streams directly to this process.

Feed streams to our process can also comprise effluent streams from processes which have removed varying amounts of one or more xylene isomers. As one example, at least a portion of the ortho-xylene may have been previously removed by fractionation from a feed mixture containing the xylene isomers. Ortho-xylene has a boiling point of about 5° F. higher than that of the nearest other $C_8$ aromatic (meta-xylene) and hence can be removed as a bottoms product from ortho-xylene fractionator towers. Such towers will typically contain about 100 to 105 actual trays and will operate with about a 5–8 to 1 reflux to feed ratio. The concentration of ortho-xylene in the effluent or overhead from this fractionation process which can be used as a feedstream to our process will then be less than the concentrations of either para-xylene or meta-xylene. Alternatively at least a portion of the para-xylene may have been previously removed from a feed mixture containing the xylene isomers by a fractional crystallization process or by a solid-bed selective adsorptive process or by a combination of both. In this situation, the concentration of para-xylene in the effluent which is now charged as a feed stream to our process will be less than the concentrations of either ortho-xylene or meta-xylene. As another alternative, perhaps at least a portion of both ortho- and para-xylene will have been previously removed, by the processes described above, from a feed mixture containing the xylene isomers. The concentration of both ortho-xylene and para-xylene in this feed stream to our process would then each be less than that of meta-xylene.

Feed mixtures may also contain small quantities of non-aromatics such as straight or branched chain paraffins, cycloparaffins, or olefinic materials. However, since separation of ethylbenzene from a feed mixture by selective adsorption of the xylenes present in the feed mixture on a zeolite adsorbent apparently takes place because of a rather delicate acidity/basicity difference between the xylene isomers and the adsorbent compared to that between ethylbenzene and the adsorbent, it is preferred that these contaminants, especially olefins, be less than about 20 vol. % of the feed mixture passed into the process and more preferably be less than about 10 vol. %, so that this difference is not upset. Another reason for having minimum concentrations of non-aromatics in the feed mixture is that all unadsorbed components will appear in the raffinate stream along with ethylbenzene. Unless these components are later removed from the raffinate stream the purity of the ethylbenzene will be decreased.

To separate ethylbenzene from a feed mixture containing ethylbenzene and at least one xylene isomer, the mixture is contacted with the particular adsorbent and the xylene isomers are more selectively adsorbed and retained by the adsorbent while the less selectively adsorbed ethylbenzene is removed from the interstitial void spaces between the particles of adsorbent and the surface of the adsorbent. The adsorbent containing the more selectively adsorbed xylene isomers is referred to as a "rich" adsorbent—rich in the more selectively adsorbed xylene isomers.

A more selectively adsorbed isomer is commonly referred to as an extract component of the feed mixture, while a less selectively adsorbed component is referred to as a raffinate component. Fluid streams leaving the adsorbent comprising an extract component and comprising a raffinate component are referred to, respectively, as the extract stream and the raffinate stream. Since all of the xylene isomers will be selectively adsorbed with respect to ethylbenzene, the extract stream will contain as extract components all of the xylene isomers appearing in the feed mixture and the raffinate stream will contain essentially only ethylbenzenes as the raffinate component.

Although it is possible by the process of this invention to produce high purity (98% or greater, expressed as a percent of $C_8$ aromatics present) ethylbenzene at high recoveries (95% or greater), it will be appreciated that an extract component is never completely adsorbed by the adsorbent, nor is a raffinate component completely non-adsorbed by the adsorbent. Therefore, small amounts of a raffinate component can appear in the extract stream and, likewise, small amounts of an extract component can appear in the raffinate stream. The extract and raffinate streams then are further distinguished from each other and from the feed mixture by the ratio of the concentration of the $C_8$ aromatic isomers appearing in the particular stream. More specifically, the ratio of the concentration of a more selectively adsorbed xylene isomer to that of the less selectively adsorbed ethylbenzene will be lowest in the raffinate stream, next highest in the feed mixture, and the highest in the extract stream. Likewise, the ratio of the concentration of the less selectively adsorbed ethylbenzene to that of a more selectively adsorbed xylene isomer will be highest in the raffinate stream, next highest in the feed mixture, and the lowest in the extract stream.

The adsorbent can be contained in one or more chambers where through programed flow into and out of the chamber separation of the isomers is effected. The adsorbent will preferably be contacted with a desorbent material which is capable of displacing the adsorbed xylene isomers from the adsorbent. Alternatively, the adsorbed xylene isomer could be removed from the adsorbent by purging or by increasing the temperature of the adsorbent or by decreasing the pressure of the chamber or vessel containing the adsorbent or by a combination of these means.

The adsorbent may be employed in the form of a dense compact fixed bed which is alternatively contacted with the feed mixture and a desorbent material (hereinafter described in more detail). In the simplest embodiment of the invention the adsorbent is employed in the form of a single static bed in which case the process is only semi-continuous. A set of two or more static beds may be employed in fixed-bed contacting with appropriate valving so that the feed mixture is passed through one or more adsorbent beds while the desorbent material is passed through one or more of the other beds in the set. The flow of feed mixture and desorbent material may be either up or down through the desorbent. Any of the conventional apparatus employed in static bed fluid-solid contacting may be used.

Countercurrent moving-bed or simulated moving-bed countercurrent flow systems, however, have a much greater separation efficiency than fixed adsorbent bed systems and are therefore preferred. In the moving-bed or simulated moving-bed processes the adsorption and desorption operations are continuously taking place which allows both continuous production of an extract and a raffinate stream and the continual use of feed and desorbent streams. One preferred processing flow scheme which can be utilized to effect the process of this invention includes what is known in the art as the simulated moving-bed countercurrent flow system. The operating principles and sequence of such a flow system are described in U.S. Pat. No. 2,985,589 issued to D. B. Broughton. In such a system it is the progressive movement of multiple liquid access points down an adsorbent chamber that simulates the upward movement of adsorbent contained in the chamber. Only four of the access lines are active at any one time; the feed in, desorbent in, raffinate stream out, and extract stream out access lines. Coincident with this simulated upward movement of the solid adsorbent is the movement of the liquid occupying the void volume of the packed bed of adsorbent. So that countercurrent contact is maintained, a liquid flow down the adsorbent chamber is provided by a pump. As an active liquid access point moves through a cycle, that is, from the top of the chamber to the bottom, the chamber circulation pump moves through different zones which require different flow rates. A programed flow controller is provided to set and regulate these flow rates.

The active liquid access points effectively divided the adsorbent chamber into separate zones, each of which has a different function. Zone 1, bounded by the feed in and raffinate stream out access points is the adsorption zone. The adsorbent entering this zone at the raffinate out access point contains only the raffinate components and desorbent. As it rises and contacts the descending liquid which is richer in the extract components, the selectivity of the adsorbent for the extract components causes them to be adsorbed. The displaced desorbent and raffinate components are withdrawn as the raffinate stream. The adsorbent leaving the zone at the feed in access point contains all of the adsorbed species. Zone 2, bounded by the feed in and extract stream out access points, is the rectification zone. The descending liquid entering this zone, being rich in extract components and desorbent, causes the replacement of the raffinate components from the ascending adsorbent. Zone 3, bounded by the extract out and desorbent in access points, is the desorption zone. The rising adsorbent from Zone 2, containing extract components and desorbent, is contacted by the descending desorbent stream, resulting in the desorption of the extract components. The exiting extract stream contains both desorbent and extract components. Zone 4, a secondary rectification zone, is bounded by the raffinate out and desorbent in access points. Here, desorbent from the ascending adsorbent is desorbed by the raffinate components in the liquid from zone 1. The desorbent reclaimed reduces the quantity of external desorbent required to desorb the extract components in Zone 3. Fractionators are used to separate the extract and raffinate components from the desorbent in the extract and raffinate streams. A preferred embodiment of this process will utilize this simulated moving-bed countercurrent flow system.

Adsorption and desorption conditions for adsorptive separation processes can generally be either in the liquid or vapor phase or both but for aromatic isomer separation processes employing zeolitic adsorbents and the flow system described above all liquid-phase operations are usually preferred. Preferred adsorption conditions for the process of this invention will include temperatures within the range of from about 100° F. to about 450° F. and will include pressures in the range from about atmospheric to about 500 psig. Pressures higher than about 500 psig. do not appear to affect the selectivity to a measurable amount and additionally would increase the cost of the process. Desorption conditions for the process of the invention shall generally include the same range of temperatures and pressures as described for adsorption operations. The desorption of the selectively adsorbed isomer could also be effected at subatmospheric pressures or elevated temperatures or both by vacuum purging of the adsorbent to remove the adsorbed isomer but this process is not primarily directed to these desorption methods.

The desorbent materials which can be used in the various processing schemes employing this adsorbent will vary depending on the type of operation employed. The term "desorbent material" as used herein shall mean any fluid substance capable of removing a selectively adsorbed feed component from the adsorbent. In the swing-bed system in which the selectively adsorbed feed component is removed from the adsorbent by a purge stream, desorbent materials comprising gaseous hydrocarbons such as methane, ethane, etc., or other types of gases such as nitrogen or hydrogen may be used at elevated temperatures or reduced pressures or both to effectively purge the adsorbed feed component from the adsorbent.

However, in adsorptive separation processes which employ zeolitic adsorbents and which are generally operated at substantially constant pressures and temperatures to insure liquid phase, the desorbent material relied upon must be judiciously selected to satisfy several criteria. First, the desorbent material must displace the extract components from the adsorbent with reasonable mass flow rates without itself being so strongly adsorbed as to unduly prevent the extract component from displacing the desorbent material in a following adsorption cycle. Expressed in terms of the selectivity (hereinafter discussed in more detail), it is preferred that the adsorbent be more selective for all of the extract components with respect to a raffinate component than it is for the desorbent material with respect to a raffinate component. Secondly, desorbent materials must be compatible with the particular adsorbent and the particular feed mixture. More specifically, they must not reduce or destroy the critical selectivity of the adsorbent for the extract components with respect to the raffinate component.

Desorbent materials to be used in the process of this invention should additionally be substances which are easily separable from the feed mixture that is passed into the process. After desorbing the extract components of the feed, both desorbent material and the extract components are removed in admixture from the adsorbent. Likewise, the raffinate component ethylbenzene is withdrawn from the adsorbent in admixture with desorbent material. Without a method of separating desorbent material, such as distillation, the purity of neither the extract components nor the raffinate component would not be very high. It is therefore contemplated that any desorbent material used in this process will have a substantially different average boiling point than that of the feed mixture. The use of a desorbent material having a substantially different average boiling point than that of the feed allows separation of desorbent material from feed components in the extract and raffinate streams by simple fractionation thereby permitting reuse of desorbent material in the process. The term "substantially different" as used herein shall mean that the difference between the average boiling points between the desorbent material and the feed mixture shall be at least about 15° F. The boiling range of the desorbent material may be higher or lower than that of the feed mixture.

In the preferred isothermal, isobaric, liquid-phase operation of the process of our invention, we have found that desorbent materials comprising monoaromatic hydrocarbons are particularly effective. Specifically, desorbent materials comprising toluene are especially preferred for this type of operation. Mixtures of toluene with paraffins are also effective as desorbent materials. Such paraffins must be compatible with the adsorbent and feed mixture as described above and must be easily separable from the feed mixture. The paraffins can include straight or branched chain paraffins or cycloparaffins which meet these criteria. Typical concentrations of toluene in such mixtures can be from a few volume percent up to near 100 vol. % of the total desorbent material mixture but such concentrations preferably will be within the range of from about 50 vol. % to about 100 vol. % of the mixture.

With the operation of our process now in mind, one can appreciate that certain characteristics of adsorbents are highly desirable, if not absolutely necessary, to the successful operation of a selective adsorption process. Among such characteristics are: adsorptive capacity for some volume of an extract component per volume of adsorbent; the selective adsorption of extract components with respect to a raffinate component and the desorbent material; and sufficiently fast rates of adsorption and desorption of the extract compounds to and from the adsorbent.

Capacity of the adsorbent for adsorbing a specific volume of one or more extract component is, of course, a necessity; without such capacity the adsorbent is useless for adsorptive separation. Furthermore, the higher the adsorbent's capacity for an extract component the better is the adsorbent. Increased capacity of a particular adsorbent makes it possible to reduce the amount of adsorbent needed to separate the extract component contained in a particular charge rate of feed mixture. A reduction in the amount of adsorbent required for a specific adsorptive separation reduces the cost of the separation process. It is important that the good initial capacity of the adsorbent be maintained during actual use in the separation process over some economically desirable life.

The second necessary adsorbent characteristic is the ability of the adsorbent to separate components of the feed; or, in other words, that the adsorbent possess adsorptive selectivity, (B), for one component as compared to another component. Relative selectivity can be expressed not only for one feed component as compared to another but can also be expressed between any feed mixture component and the desorbent material. The selectivity, (B), as used throughout this specification is defined as the ratio of the two components of the adsorbed phase over the ratio of the same two components in the unadsorbed phase at equilibrium conditions.

Relative selectivity is shown as Equation 1 below:

EQUATION 1

$$\text{Selectivity} = (B) = \frac{[\text{vol. percent } C/\text{vol. percent } D]_A}{[\text{vol. percent } C/\text{vol. percent } D]_U} \quad \text{Equation 1}$$

where C and D are two components of the feed represented in volume percent and the subscripts A and U represent the adsorbed and unadsorbed phases respectively. The equilibrium conditions were determined when the feed passing over a bed of adsorbent did not change composition after contacting the bed of adsorbent. In other words, there was no net transfer of material occurring between the unadsorbed and adsorbed phases.

Where selectivity of two components approaches 1.0 there is no preferential adsorption of one component by the adsorbent with respect to the other; they are both adsorbed (or non-adsorbed) to about the same degree with respect to each other. As the (B) becomes less than or greater than 1.0 there is preferential adsorption by the adsorbent for one component with respect to the other. When comparing the selectivity by the adsorbent of one component C over component D, a (B) larger than 1.0 indicates preferential adsorption of component C within the adsorbent. A (B) less than 1.0 would indicate that component D is preferentially adsorbed leaving an unadsorbed phase richer in component C and an adsorbed phase richer in component D. For optimum performance desorbent materials should have a selectivity equal to about 1 or less than 1 with respect to all extract components so that all of the extract components can be extracted as a class and all raffinate components clearly rejected into the raffinate stream.

The third important characteristic is the rate of exchange of the extract component of the feed mixture material or, in other words, the relative rate of desorption of the extract component. This characteristic relates directly to the amount of desorbent material that must be employed in the process to recover the extract component from the adsorbent; faster rates of exchange reduce the amount of desorbent material needed to remove the extract component and therefore permit a reduction in the operating cost of the process. With faster rates of exchange, less desorbent material has to be pumped through the process and separated from the extract stream for reuse in the process.

In order to test various adsorbents and desorbent material with a particular feed mixture to measure the adsorbent characteristics of adsorptive capacity and selectivity and exchange rate a dynamic testing apparatus is employed. The apparatus consists of an adsorbent chamber of approximately 70 cc volume having inlet and outlet portions at opposite ends of the chamber. The chamber is contained within a temperature control means and, in addition, pressure control equipment is used to operate the chamber at a constant predetermined pressure. Chromatographic analysis equipment can be attached to the outlet line of the chamber and used to analyze "on-stream" the effluent stream leaving the adsorbent chamber.

A pulse test, performed using this apparatus and the following general procedure, is used to determine selectivities and other data for various adsorbent systems. The adsorbent is filled to equilibrium with a particular desorbent by passing the desorbent material through the adsorbent chamber. At a convenient time, a pulse of feed containing known concentrations of a non-adsorbed paraffinic tracer (n-nonane for instance) and of the particular $C_8$ aromatic isomers all diluted in desorbent is injected for a duration of several minutes. Desorbent flow is resumed, and the tracer and the aromatic isomers are eluted as in a liquid-solid chromatographic operation. The effluent can be analyzed by on-stream chromatographic equipment and traces of the envelopes of corresponding component peaks developed. Alternatively, effluent samples can be collected periodically and later analyzed separately by gas chromatography.

From information derived from the chromatographic traces, adsorbent performance can be rated in terms of capacity index for an extract component, selectivity for one isomer with respect to the other, and the rate of desorption of extract component by the desorbent. The capacity index may be characterized by the distance between the center of the peak envelope of the selectively adsorbed isomer and the peak envelope of the tracer component or some other known reference point. It is expressed in terms of the volume in cubic centimeters of desorbent pumped during this time interval. Selectivity, (B), for an extract component with respect to a raffinate component may be characterized by the ratio of the distance between the center of the extract component peak envelope and the tracer peak envelope (or other reference point) to the corresponding distance between the center of the raffinate component peak envelope and the tracer peak envelope. The rate of exchange of an extract component with the desorbent can generally be characterized by the width of the peak envelopes at high intensity. The narrower the peak width the faster the desorption rate. The desorption rate can also be characterized by the distance between the center of the tracer peak envelope and the disappearance of an extract component which has just been desorbed. The distance is again the volume of desorbent pumped during this time interval.

To further evaluate promising adsorbent systems and to translate this type of data into a practical separation process requires actual testing of the best system in a continuous countercurrent liquid-solid contacting device. The general operating principles of such a device have been previously described and are found in Broughton U.S. Pat. No. 2,985,589. A specific laboratory-size apparatus utilizing these principles is described in deRosset et al U.S. Pat. No. 3,706,812. The equipment comprises multiple adsorbent beds with a number of access lines attached to distributors within the beds and terminating at a rotary distributing valve. At a given valve position, feed and desorbent are being introduced through two of the lines and the raffinate and extract streams are being withdrawn through two more. All remaining access lines are inactive and when the position of the distributing valve is advanced by one index all active positions will be advanced by one bed. This simulates a condition in which the adsorbent physically moves in a direction countercurrent to the liquid flow. Additional details on the above-mentioned adsorbent testing apparatus and adsorbent evaluation techniques may be found in the paper "Separation of $C_8$ Aromatics by Adsorption" by A. J. deRosset, R. W. Neuzil, D. J. Korous, and D. H. Rosback presented at the American Chemical Society, Los Angeles, California, March 28 through April 2, 1971.

The feasibility of separating ethylbenzene from a feed mixture comprising ethylbenzene and a plurality of xylene isomers by selective adsorption of the xylene isomers on the particular adsorbent disclosed herein, which was demonstrated by pulse test results, was confirmed by continuous testing in the laboratory-sized apparatus described above.

Adsorbents to be used in the process of this invention will comprise specific crystalline aluminosilicates or molecular sieves. Particular crystalline aluminosilicates encompassed by the present invention include crystalline aluminosilicate cage structures in which the alumina and silica tetrahedra are intimately connected in an open three dimensional network. The tetrahedra are cross-linked by the sharing of oxygen atoms with spaces between the tetrahedra occupied by water molecules prior to partial or total dehydration of this zeolite. The dehydration of the zeolite results in crystals interlaced with cells having molecular dimensions. Thus, the crystalline aluminosilicates are often referred to as "molecular sieves" when the separation which they effect is dependent essentially upon differences between the sizes of the feed molecules as, for instance, when smaller normal paraffin molecules are separated from larger isoparaffin molecules by using a particular molecular sieve. In the process of this invention, however, the term "molecular sieves" although widely used is not strictly suitable since the separation of specific $C_8$ aromatic isomers is dependent on differences in electrochemical attraction of the different isomers and the adsorbent rather than on pure physical size differences in the isomer molecules.

In hydrated form, the crystalline aluminosilicates generally encompass those zeolites represented by the Formula 1 below:

FORMULA 1

$$M_{2/n}O:Al_2O_3:wSiO_2:yH_2O$$

where "M" is a cation which balances the electrovalence of the tetrahedra and is generally referred to as an exchangeable cationic site, n represents the valence of the cation, w represents the moles of $SiO_2$, and y represents the moles of water. The cation M may be one or more of a number of possible cations.

The prior art has generally recognized that adsorbents comprising the type X structured and the type Y structured zeolites can be used in certain adsorptive separation processes. These zeolites are described and defined in U.S. Pat. Nos. 2,882,244 and 3,120,007 respectively. The terms "type X structured" and "type Y structured" zeolites as used herein shall include all zeolites which have general structures as represented in the above two cited patents.

The type X structured zeolite in the hydrated or partially hydrated form can be represented in terms of mole oxides as shown in Formula 2 below:

FORMULA 2

$$(0.9\pm0.2)M_{2/n}O:Al_2O_3:(2.5\pm0.5)SiO_2:yH_2O$$

a sodium-type
where M represents at least one cation having a valence of not more than 3, n represents the valence of M, and y is a value up to about 9 depending upon the identity of M and the degree of hydration of the crystal. As noted from Formula 2 the $SiO_2/Al_2O_3$ mole ratio is 2.5±0.5. The cation M may be one or more of a number of cations such as the hydrogen cation, the alkali metal cation, or the alkaline earth cations, or other selected cations, and is generally referred to as an exchangeable cationic site. As the type X zeolite is initially prepared, the cation M is usually predominately sodium and the zeolite is therefore referred to as a sodium type X zeolite. Depending upon the purity of the reactants used to make the zeolite, other cations mentioned above may be present, however, as impurities.

The type Y structured zeolite in the hydrated or partially hydrated form can be similarly represented in terms of mole oxides as in formula 3 below.

FORMULA 3

$$(0.9\pm0.2)M_{2/n}O:Al_2O_3:wSiO_2:yH_2O$$

where M is at least one cation having a valence not more than 3, n represents the valence of M, W is a value greater than about 3 up to 8, and y is a value up to about 9 depending upon the identity of M, and the degree of hydration of the crystal. The $SiO_2/Al_2O_3$ mole ratio for type Y structured zeolites can thus be from about 3 to about 8. Like the type X structured zeolite, the cation M may be one or more of a variety of cations but, as the type Y zeolite is initially prepared, the cation M is also usually predominately sodium. The type Y zeolite containing predominately sodium cations at the exchangeable cationic sites is therefore referred to as a sodium-type Y zeolite.

Cations occupying exchangeable cationic sites in the zeolite may be replaced with other cations by ion exchange methods generally known to those having ordinary skill in the field of crystalline aluminosilicates. Such methods are generally performed by contacting the zeolite with an aqueous solution of the soluble salt of the cation or cations desired to be placed upon the zeolite. After the desired degree of exchange takes place the sieves are removed from the aqueous solution, washed, and dried to a desired water content. By such methods the sodium cations and any non-sodium cations which might be occupying exchangeable sites as impurities in a sodium-type X or sodium-type Y zeolite can be partially or essentially completely replaced with other cations.

For the particular separation process of this invention where ethylbenzene is to be recovered in high purity as a raffinate component it is necessary that the zeolitic adsorbent possess selectivity for all of the xylene isomers with respect to ethylbenzene so that ethylbenzene will be rejected rather than adsorbed by the adsorbent. While separation is theoretically possible when all of the xylene selectivities with respect to ethylbenzene are greater than 1, it is preferred that such selectivities be at least equal to 2. Like relative volatility, the higher the selectivity, the easier the separation is to perform. Higher selectivities permit a smaller amount of adsorbent to be used. Moreover, the selectivities for the three xylenes with respect to ethylbenzene should all be about the same to permit extraction of the xylenes cleanly as a class. To separate ethylbenzene in high purities and at high recoveries, especially when the ethylbenzene concentration in the feed is less than or about the same as that of para-xylene, it is also necessary that the adsorbent possess selectivities for all of the xylene isomers with respect to ethylbenzene which are greater than the selectivity of the desired desorbent material with respect to ethylbenzene. While the deleterious effect (lower recoveries or yields of ethylbenzene) of a strongly held desorbent material is substantially reduced or eliminated if the ethylbenzene concentration is higher than that of para-xylene. It is desirable that the process be able to separate ethylbenzene in high purity and at high recovery from a variety of possible feeds including those in which the ethylbenzene concentration is less than or about the same as that of para-xylene.

We have found that for the process of this invention adsorbents comprising strontium and potassium exchanged type X or Y zeolites satisfy these selectivity requirements and the other adsorbent requirements previously discussed. The adsorbent for our process will typically comprise strontium and potassium exchanged type X or Y zeolite in concentrations generally ranging from about 75 wt. % to about 98 wt. % of the adsorbent based on a volatile free composition. The remaining material in the adsorbent will generally comprise amorphous silica or alumina or both present in intimate mixture with the zeolite material to aid in forming the zeolite into particles of the desired size. This amorphous material may be an adjunct of the manufacturing process of the type X or Y zeolite (for example, intentionally incomplete purification of the zeolite during its manufacture) or it may be added to the relatively pure zeolite to aid in forming the zeolite into such particles as extrudates, aggregates, tablets, pills, or macrospheres. The adsorbent for our process will preferably be smaller particles in about 20 to 40 U.S. mesh particle size range which can be produced by grinding and screening the larger aforementioned particles.

Suitable adsorbents can be prepared by ion exchanging sodium-type X or type Y zeolites to the desired strontium and potassium content. A zeolite commercially available from the Linde Company, Tonawanda, New York, under the trade name "Molecular Sieves 13X" can, for instance, be ion exchanged with strontium and potassium to produce a suitable adsorbent. Cationic or base exchange methods are generally well known to those skilled in the art of crystalline aluminosilicate production. They are generally performed by contacting the zeolite with an aqueous solution of the soluble salts of the cation or cations desired to be placed upon the zeolite. The desired degree of exchange takes place and then the sieves are removed from the aqueous solution, washed and dried to a desired water content. While an adsorbent comprising type X or Y zeolite which has been partially exchanged with strontium and potassium can be employed in our process, we have found that adsorbents comprising type X or Y zeolites which are essentially completely exchanged with strontium and potassium are preferred. A type X or Y zeolite is herein deemed to be essentially completely exchanged when the residual sodium content of the zeolite, reported as $Na_2O$, is less than about 2.0 wt. %. It is contemplated that cation exchange operations may take place using individual solutions of desired cations to be placed on the zeolite or using an exchange solution containing a mixture of cations, where two or more desired cations are to be placed on the zeolite.

In addition to the degree of completeness of the ion exchange, one can also vary the concentrations of individual cations exchanged into the zeolite. In the process of this invention, we have found that relatively small amounts of potassium in the zeolite enhance the transfer rates and produce an adsorbent more uniformly selective for the three xylenes with respect to ethylbenzene thus permitting all of the xylenes to be cleanly extracted as a class with no tailing of any one isomer during desorption into the ethylbenzene product. The relative amounts of strontium to potassium can be best characterized by the weight ratio of strontium to potassium present in the adsorbent. Typically, weight ratios of strontium to potassium present on the adsorbent can range from about 1 up to about 275. In this broad range the weight percent potassium in the adsorbent will typically be from about 0.1 to about 10 wt. % $K_2O$ and that of strontium in the adsorbent from about 20 to about 27 wt. % SrO. More preferably however, the weight ratio of strontium to potassium will be within the range of from about 1 to about 100. An especially preferred range is a strontium to potassium weight ratio of from about 5 to about 50 with a range of from about 5 to about 25 being even more preferred.

While water has the same effect upon transfer rates as does potassium, the disadvantage is that a relatively high adsorbent water content must be maintained during the use of the adsorbent to achieve this effect. When the adsorbent contains potassium in amounts described above, the process can be operated at a much lower adsorbent water content and maintaining water content during the operation is not as critical to achieve optimum adsorbent performance. The effects of water content and potassium content on adsorbent performance are shown in Table 2 below.

Table 2

| EFFECT OF ADSORBENT WATER CONTENT AND POTASSIUM CONTENT ON ADSORBENT PERFORMANCE | | | | | | | |
|---|---|---|---|---|---|---|---|
| Adsorbent | A | B | C | D | E | F | G |
| wt. % $K_2O$ | 0 | 0 | 0 | 0 | 4.4 | 4.4 | 4.4 |
| LOI at 500° C. | 0 | 1 | 3 | 4 | 0 | 1 | 2 |
| Pulse Test No. | 1 | 2 | 3 | 4 | 5 | 6 | 7 |
| Selectivities: | | | | | | | |
| p/e | 1.93 | 2.32 | 2.06 | 2.08 | 2.34 | 2.18 | |
| | 2.35 | | | | | | |
| m/e | 3.20 | 3.18 | 2.90 | 2.71 | 2.96 | 2.70 | 2.45 |
| o/e | 2.55 | 2.35 | 2.32 | 2.24 | 2.21 | 2.19 | 2.04 |
| m-xylene peak envelope width, cc | 13.7 | 15.3 | 13.1 | 11.2 | 13.3 | 13.4 | 12.5 |

Table 2 shows results of seven pulse tests made on adsorbents A through G. Adsorbents A, B, C and D were portions of an adsorbent prepared by essentially completely exchanging linde 13X molecular sieves with strontium. Adsorbents E, F, and G were prepared by exchanging the strontium-exchanged adsorbent with potassium to a $K_2O$ content of 4.4 wt. %. The adsorbents as prepared were approximately 20–40 U.S. mesh particle size range and were dried to essentially 0 wt. % loss on ignition (LOI) at 500° C. Adsorbent portions B, C, D, F, and G were rehydrated to the water contents shown by passing wet nitrogen through beds of the particular adsorbent portions; adsorbents A and E contained essentially no water as measured by LOI at 500° C.

The testing apparatus was an adsorbent chamber containing approximately 70 cc of each adsorbent and contained within a temperature-controlled means in order to maintain essentially isothermal operations through the column. For each pulse test the column was maintained at a temperature of 150° C. and a pressure of 100 psig. to maintain liquid-phase operations. Gas chromatographic analysis equipment was attached to the column effluent stream in order to determine the composition of the effluent material at given time intervals. The feed mixture employed for each test contained 5 vol. % each ethylbenzene, para-xylene, meta-xylene, ortho-xylene, and n-nonane (used as a tracer) and 75 vol. % toluene. The desorbent material was toluene. The operations taking place for each test were as follows. The desorbent material was run continuously at a nominal liquid hourly space velocity (LHSV) of 1.0 which amounted to about 1.17 cc per minute feed rate of desorbent. At some convenient time interval the desorbent was stopped and the feed mixture was run for a ten-minute interval at 1 LHSV. The desorbent stream was then resumed at 1 LHSV and continued to pass into the adsorbent column until all of the feed $C_8$ aromatics had been eluted from the column as determined by observing the chromatograph generated by the effluent material leaving the adsorption column. The sequence of operations usually takes about an hour. The 10 minute pulse of feed and subsequent desorption may be repeated in sequence as often as is desired. From information derived from the chromatographic traces selectivities of the adsorbents for the xylene isomers with respect to ethylbenzene (p/e, m/e, and o/e) and the envelope peak width for meta-xylene were calculated, by the methods previously described, for each pulse test.

Results for test 1 with adsorbent A which contained 0 wt. % $K_2O$ and 0 wt. % LOI at 500° C. show a wide spread between the m/e selectivity (3.20) and the p/e selectivity (1.39) indicating that meta-xylene will tend to be desorbed with more difficulty than para-xylene or ortho-xylene and may thus tend to "tail" into the ethylbenzene-containing raffinate stream thereby reducing the ethylbenzene purity. The spread decreases with increasing water content and the most uniform selectivities were obtained for tests 3 and 4 at an adsorbent water content of from 3 to 4 wt. %. At this water content the adsorbent is more uniformly selective for the three xylenes with respect to ethylbenzene thus permitting all of the xylenes to be cleanly extracted as a class with no tailing of any one xylene isomer into the ethylbenzene product. The faster transfer rates at the 3 to 4 wt. % level are also indicated by the narrower meta-xylene peak envelope widths obtained during tests 3 and 4. Results for test 5 with adsorbent E which contained 4.4 wt. % $K_2O$ and 0 wt. % LOI at 500° C. and for test 6 with adsorbent F which contained 4.4 wt. % $K_2O$ and 1 wt. % LOI at 500° C. show narrower spreads between the m/e selectivity and the p/e selectivity than those of tests 1 and 2 with adsorbents having the same water content but no potassium. The most uniform selectivities were obtained for tests 6 and 7 at an adsorbent water content of from 1 to 2 wt. % LOI at 500° C. Moreover, the spread between m/e and p/e selectivities was smaller for these tests with adsorbents F and G having water contents of 1 and 2 wt. % LOI at 500° C. respectively than it was for tests 3 and 4 with adsorbents C and D which had higher water contents of 3 and 4 wt. % LOI at 500° C. respectively. A comparison of selectivities for test 5 with those of test 1 shows that even if the water content of an adsorbent comprising Sr-K exchanged zeolite containing 1–2 wt. % LOI at 500° C. were allowed to decrease to about 0 wt. % LOI the adsorbent performance is better than if the water content of an adsorbent comprising a Sr-exchanged zeolite were similarly allowed to decrease to about 0 wt. % LOI. Thus the data illustrates that an adsorbent comprising strontium and potassium exchanged zeolite is more uniformly selective for the three xylenes isomers at a lower water content than an adsorbent comprising a strontium exchanged zeolite and that water content is not as critical to acceptable adsorbent performance as it is for an adsorbent comprising a strontium-exchanged zeolite.

Although the adsorbent comprising strontium and potassium exchanged X and Y zeolite having a water content of essentially 0 wt. % LOI at 500° C. can be used in our process, it is preferred that adsorbent water content be monitored and controlled to achieve optimum adsorbent performance. This is especially true of a commercial-sized process which contains a large quantity of adsorbent and which remains on-stream for long periods of time. The adsorbent water content will initially be adjusted to the desired level as part of the manufacturing method or may be adjusted after loading into the chambers before actual process operation is begun. Thereafter the known initial water content of the zeolite may be monitored by sampling the input streams (feed and desorbent material) and output streams (extract and raffinate) and analyzing them for water content by methods well known to the petroleum and petrochemical industry. The water content of the adsorbent can then be calculated by water balance. If the water content is too low it may be increased by adding water to the adsorbent either on an intermittent or more preferably on a continuous basis by itself or in admixture with feed or desorbent material. If the water content is too high, passing the desorbent material or feed or both through a dryer and letting the output streams remove some water will reduce it to the proper range.

The following examples are presented to illustrate the present invention and are not intended to unduly restrict the scope and spirit of the claims attached hereto. More specifically the examples demonstrate the advantage of this process over a process using an adsorbent comprising calcium-exchanged type X or Y zeolite and toluene as desorbent material when the concentration of ethylbenzene is lower than or about the same as that of para-xylene.

EXAMPLE I

This example illustrates the reason why the process of our invention can produce high yields of high purity ethylbenzene for any concentration of ethylbenzene in the feed. In this example pulse tests were run on an adsorbent comprising calcium exchanged type X zeolite (Ca-X) and on an adsorbent comprising strontium and potassium exchanged type X zeolite (Sr-K-X) using the pulse test apparatus, procedure, feed and desorbent material previously described. The Sr-K-X adsorbent was prepared from Linde 13X Molecular Sieves. The Ca-X adsorbent was Linde 10X Molecular Sieves. Selectivities for the three xylene isomers (p, m, and o) and toluene with respect to ethylbenzene are shown below in Table 3.

Table 3

Comparative Selectivities for Ca—X and Sr—K—X Adsorbents

| Adsorbent Selectivities: | Ca—X | Sr—K—X |
|---|---|---|
| p/e | 2.27 | 2.32 |
| m/e | 3.57 | 2.92 |
| o/e | 2.97 | 2.35 |
| Toluene/e | 2.61 | 1.82 |

The data shows that for the Ca-X adsorbent the toluene/e selectivity is higher than the p/e selectivity and less than the m/e and o/e selectivities but that for the Sr-K-X adsorbent the toluene/e selectivity is less than the p/e selectivity or any other xylene selectivity. Thus the Sr-K-X adsorbent, in contrast to the Ca-X adsorbent, will permit clean adsorption and desorption of all the xylenes as a class thereby making separation of ethylbenzene in high yields as well as high purity possible.

EXAMPLE II

This example illustrates the ability of our process when operated in its preferred embodiment as a continuous simulated moving bed countercurrent flow type of operation to separate ethylbenzene in high purity at high recovery from a feed containing ethylbenzene at a concentration equal to or less than that of para-xylene.

The example presents test results obtained with Ca-X and Sr-K-X adsorbents in a pilot plant scale testing apparatus, known as a carousel unit, described in detail in deRosset et al U.S. Pat. No. 3,706,816. Briefly, the apparatus consists essentially of 24 serially connected adsorbent chambers having about 44 cc volume each. Total chamber volume of the apparatus is approximately 1,056 cc. The individual adsorbent chambers are serially connected to each other with relatively small-diameter connecting piping and to a rotary type valve with other piping. The valve has inlet and outlet ports which direct the flow of feed and desorbent material to the chambers and extract and raffinate streams from the chambers. By manipulating the rotary valve and maintaining given pressure differentials and flow rates through the various lines passing into and out of the series of chambers, a simulated countercurrent flow is produced. The adsorbent remains stationary while fluid flows throughout the serially connected chambers in a manner which when viewed from any position within the adsorbent chambers is steady countercurrent flow. The moving of the rotary valve is done in a periodic shifting manner to allow a new operation to take place in the adsorbent beds located between the active inlet and outlet ports of the rotary valve. Attached to the rotary valve are input lines and output lines through which fluids to and from the process flow. The rotary valve contains a feed input line through which passes a feed mixture containing ethylbenzene and xylene isomers, an extract stream outlet line through which passes desorbent material in admixture with the xylene isomers, a desorbent material inlet line through which passes desorbent materials and a raffinate stream outlet line through which passes ethylbenzene in admixture with desorbent material. Additionally, a flush material inlet line is used to admit flush material for the purpose of flushing feed components from lines which had previously contained feed material and which will subsequently contain the raffinate or extract stream. The flush material employed is desorbent material which then leaves the apparatus as part of the extract stream and raffinate stream. Additional apparatus details can be found in U.S. Pat. No. 3,706,812. In order to better understand the operations taking place within the apparatus, reference can be made to D. B. Broughton U.S. Pat. 2,985,589 and to D. B. Broughton et al, "The Separation of P-Xylene from $C_8$ Hydrocarbon Mixtures by the Parex Process," presented at the Third Joint Annual Meeting, American Institute of Chemical Engineers and Puerto Rican Institute of Chemical Engineers, San Juan, Puerto Rico, May 17 through May 20, 1970. These references describe in detail the basic operations taking place in the testing apparatus used in this Example.

Operating temperature and pressure during the tests were 150° C. and 150 psig. respectively. The desorbent material used was toluene. Four feed materials were used, two of them having ethylbenzene concentrations higher than the para-xylene concentrations and two of them having ethylbenzene concentrations about the same or less than the para-xylene concentrations. The analyses of the feed materials used are shown in Table 4 below.

The adsorbent comprising Ca-type X zeolite was Linde 10X Molecular Sieves of approximately 20–40 U.S. Mesh particle size range. The adsorbent comprising Sr-K type X zeolite was prepared from Linde 13X Molecular Sieves in the following manner. A 2.1 liter sample of Linde 13X Molecular Sieves in approximately 20–40 U.S. mesh particle size range was prewet and washed with 5 liters water at 60° C. The ion exchange was made by pumping 62 liters of 0.075 M $Sr^{++}$ upflow at 1.3 liters/hour and 60° C. The void volumes were flushed downflow with 2 liters of deionized water at 25° C. followed by upflow washing for 2 hours at 2 liter/hour and 45° C. A 1.0 liter sample of the Sr-exchanged material was then ion exchanged with potassium by recycling 5 liters of 0.248 M $K^+$ solution at a flow rate of 2 liters per hour over the sample at 50° C. for 40 hours. The void volumes were flushed downflow with 2 liters of 25° C. deionized water followed by upflow washing with 2 liters deionized water in 1 hour and another 2 liters in 2 hours all at 60° C. After surface drying the exchanged material, the adsorbent was further dried in a muffle furnace starting at 25° C. and increasing to 500° C. in ½ hour. The drying was continued at 500° C. for ½ hour. The adsorbent analyzed 42.63 wt. % $SiO_2$, 29.16 wt. % $Al_2O_3$, 1.04 wt. % $Na_2O$, and 21.10 wt. % SrO, and 4.40 wt. % $K_2O$. Based upon the alumina analysis, the adsorbent was 91.8 mole % exchanged. The apparatus was loaded first with the Ca-X adsorbent and then the Sr-K-X adsorbent. After each loading, the adsorbents were then dried for 20 hours with 2.5 gm mol/hr of vapor phase toluene at 150° C. and atmospheric pressure. After the drying the adsorbent was rehydrated to known water contents by passing wet nitrogen from a water bubbler over the adsorbent beds.

Two tests with each adsorbent were run, one with a feed having a relatively high concentration of ethylbenzene with respect to para-xylene and the other with a relatively low ethylbenzene concentration. The four tests, run at continuous steady-state conditions, were performed to determine the ethylbenzene purity and recovery relationships obtainable with feed materials having relatively high and low ethylbenzene concentrations. "Recovery" is determined by calculating the amount of ethylbenzene which is lost through the extract stream, determining this quantity as a percentage of the ethylbenzene fed into the process and subtracting this percentage from 100 percent. Recovery then represents the percentage of ethylbenzene fed to the process which is not lost to the extract stream. Distribution of the $C_8$ aromatics in the feed, extract and raffinate was determined by gas chromatography. The test results are shown in Table 4 below.

Table 4

| Test | CAROUSEL TEST RESULTS | | | |
|---|---|---|---|---|
| | 1 | 2 | 3 | 4 |
| Adsorbent | Ca—X | Ca—X | Sr—K—X | Sr—K—X |
| Feed | | | | |
| Distribution of $C_8$ Aromatics | | | | |
| e, vol. % | 32.0 | 20.0 | 21.6 | 19.3 |
| p, vol. % | 14.3 | 20.5 | 16.8 | 19.7 |
| m, vol. % | 33.3 | 44.2 | 47.2 | 46.0 |
| o, vol. % | 20.4 | 15.3 | 14.4 | 15.0 |
| Extract Stream | | | | |
| Distribution of $C_8$ Aromatics | | | | |
| e, vol. % | 2.8 | 12.4 | 0.1 | 0.3 |
| p, vol. % | 19.7 | 22.2 | 28.2 | 26.3 |
| m, vol. % | 48.1 | 49.9 | 52.2 | 64.9 |
| o, vol. % | 29.4 | 15.5 | 19.5 | 20.5 |
| Raffinate Stream | | | | |
| Distribution of $C_8$ Aromatics | | | | |
| e, vol. % | 98.2 | 98.7 | 99.2 | 99.7 |
| p, vol. % | Tr | 0.4 | 0.2 | Tr |
| m, vol. % | 0.3 | 0.8 | 0.4 | 0.3 |
| o, vol. % | 1.5 | 0.1 | 0.2 | Tr |
| Recovery of ethylbenzene in Raffinate, % | 98.6 | 34.1 | 99.0 | 99.0 |

In test 1 ethylbenzene was separated at high purity (98.2 vol. %) and at high recovery (98.6%). The deleterious effect of the strongly held toluene desorbent material has in this test been essentially eliminated because ethylbenzene is at a high enough concentration in Zone I to displace a large portion of the toluene from the pores of the adsorbent carried in from Zone IV. Consequently the para-xylene can more readily displace the ethylbenzene from the pores higher up in Zone I and thus prevent any from getting into the extract as happens when there is a high concentration of toluene in the pores. This loss of ethylbenzene into the extract is shown by the results of test 2 where a feed containing an ethylbenzene concentration less than that of para-xylene was used. Although the purity was high (98.7 vol. %), the recovery was very low; 34.1%. For tests 3 and 4 with the Sr-K-type X adsorbent on the other hand ethylbenzene was separated at both high purity and at high recovery for feeds containing concentrations of ethylbenzene higher than and about the same as that of para-xylene.

We claim as our invention:

1. A process for separating ethylbenzene from a feed mixture comprising ethylbenzene and a plurality of xylene isomers which comprises contacting at adsorption conditions said mixture with an adsorbent comprising type X or type Y zeolite essentially completely exchanged with strontium and potassium, selectively adsorbing substantially all of said xylene isomers to the substantial exclusion of ethylbenzene, and thereafter recovering ethylbenzene.

2. The adsorbent of claim 1 further characterized in that the adsorbent contains strontium and potassium in a weight ratio of strontium to potassium of from about 1 to about 275.

3. The process of claim 1 further characterized in that said adsorbent contains from about 0 to about 2.0 wt. % water measured by loss on ignition at 500° C.

4. The process of claim 1 further characterized in that said feed mixture contains para-xylene, meta-xylene, and ortho-xylene.

5. The process of claim 4 further characterized in that the concentration of ortho-xylene in said feed mixture is less than the concentration of either para-xylene or meta-xylene.

6. The process of claim 4 further characterized in that the concentration of para-xylene in said feed mixture is less than the concentrations of either ortho-xylene or meta-xylene.

7. The process of claim 4 further characterized in that the concentrations of ortho-xylene abd para-xylene in said feed mixture are each less than the concentration of meta-xylene.

8. The process of claim 1 further characterized in that said feed mixture contains two xylene isomers.

9. The process of claim 1 including the step of treating the adsorbent containing said isomers with a desorbent material to remove the adsorbed xylenes therefrom as a fluid extract stream.

10. The process of claim 9 further characterized in that said desorbent material has an average boiling point substantially different from that of the feed mixture.

11. The process of claim 9 further characterized in that said desorbent material comprises toluene.

12. The process of claim 1 further characterized in that said adsorption conditions include a temperature within the range of from about 70° F. to about 450° F. and at a pressure within the range of from about atmospheric to about 500 psig.

13. The process of claim 12 further characterized in being effected in the liquid phase.

14. A process for separating ethylbenzene from a feed mixture comprising ethylbenzene and a plurality of xylene isomers which process comprises the steps of:
  a. contacting at adsorption conditions said mixture with an adsorbent comprising type X or type Y zeolite essentially completely exchanged with strontium and potassium and adsorbing substantially all of said xylene isomers to the substantial exclusion of ethylbenzene;

b. withdrawing from the adsorbent a raffinate stream comprising ethylbenzene;

c. contacting the adsorbent at desorption conditions with a desorbent material having a boiling point substantially different from that of the feed mixture to effect the removal of the xylene isomers; and d. withdrawing from the adsorbent an extract stream comprising said xylene isomers.

15. The process of claim 14 further characterized in that said adsorbent contains strontium and potassium in a weight ratio of strontium to potassium of from about 1 to about 275.

16. The process of claim 14 further characterized in that said adsorbent contains from about 0 to about 2.0 wt. % water measured by loss on ignition at 500° C.

17. The process of claim 14 further characterized in that said feed mixture contains para-xylene.

18. The process of claim 17 further characterized in that the concentration of ethylbenzene is less than or equal to that of para-xylene.

19. The process of claim 17 further characterized in that the concentration of ethylbenzene is greater than that of para-xylene.

20. The process of claim 14 further characterized in that said feed mixture contains para-xylene, meta-xylene, and ortho-xylene.

21. The process of claim 20 further characterized in that the concentration of ortho-xylene in said feed mixture is less than the concentrations of either para-xylene or meta-xylene.

22. The process of claim 20 further characterized in that the concentration of para-xylene in said feed mixture is less than the concentrations of either ortho-xylene or meta-xylene.

23. The process of claim 20 further characterized in that the concentrations of ortho-xylene and para-xylene in said feed mixture are each less than the concentration of meta-xylene.

24. The process of claim 14 further characterized in that said feed mixture contains two xylene isomers.

25. The process of claim 14 further characterized in that said desorbent material comprises toluene.

26. The process of claim 14 further characterized in that said adsorption conditions and desorption conditions include a temperature within the range of from about 70° F. to about 450° F. and a pressure within the range of from about atmospheric to about 500 psig.

27. The process of claim 26 further characterized in being effected in the liquid phase.

* * * * *